United States Patent [19]
Held

[11] Patent Number: 5,963,318
[45] Date of Patent: Oct. 5, 1999

[54] METHOD OF AND APPARATUS FOR PERFORMING FIXED PATHLENGTH VERTICAL PHOTOMETRY

[75] Inventor: Paul G. Held, Burlington, Vt.

[73] Assignee: Bio-Tek Holdings, Inc., Winooski, Vt.

[21] Appl. No.: 09/130,881

[22] Filed: Aug. 7, 1998

[51] Int. Cl.[6] .................................................. G01N 21/01
[52] U.S. Cl. ........................ 356/244; 356/246; 356/236
[58] Field of Search .................................. 356/244, 246, 356/236

[56] References Cited

U.S. PATENT DOCUMENTS

| | | |
|---|---|---|
| 4,278,887 | 7/1981 | Lipshutz et al. . |
| 4,405,235 | 9/1983 | Rossiter . |
| 4,656,009 | 4/1987 | Benajam . |
| 4,741,619 | 5/1988 | Humphries et al. . |
| 4,802,761 | 2/1989 | Bowen et al. . |
| 4,828,386 | 5/1989 | Matkovich et al. . |
| 5,002,889 | 3/1991 | Klein . |
| 5,073,029 | 12/1991 | Eberly et al. . |
| 5,281,394 | 1/1994 | Holub . |
| 5,434,664 | 7/1995 | Sapp ........................................ 356/244 |
| 5,774,209 | 6/1998 | Shestock ................................. 356/244 |

OTHER PUBLICATIONS

"SPECTRAmax PLUS", MDC SPECTRAmax PLUS, http://www.moldev.com/Pages/specplus.html, 5 pgs.

Primary Examiner—Frank G. Font
Assistant Examiner—Reginald A. Ratliff
Attorney, Agent, or Firm—Sughrue, Mion, Zinn, Macpeak & Seas, PLLC

[57] ABSTRACT

A system for performing vertical spectrophotometric determinations uses a vessel which has an upper transparent surface and a lower transparent surface which are spaced apart to define a known fixed pathlength through which a light beam is transmitted. The vessel also includes a portion disposed above the upper surface which may be a spout having an opening for allowing the introduction of substances into the containment portion.

20 Claims, 8 Drawing Sheets

Fig. 1

PRIOR ART

Fig. 2

PRIOR ART

Fig. 7 ered to the substance, as is the case with horizontal spectrophotometry, highly precise absorption measurements can be made using horizontal spectrophotometry.

METHOD OF AND APPARATUS FOR PERFORMING FIXED PATHLENGTH VERTICAL PHOTOMETRY

BACKGROUND OF THE INVENTION

1. Field of the Invention

The present invention relates generally to a method of and device for performing vertical spectrophotometric determinations, and, more particularly, a method of and device for performing vertical spectrophotometric determinations of a substance based on a fixed beam pathlength. The invention further relates to a method of and device for performing spectrophotometric determinations of substances using vertical beam spectrophotometric based instrumentation such as a microplate reader.

2. Description of the Background

The microplate industry has for some time used beam photometry to perform spectrophotometric determinations on liquid samples. This methodology is based on the transmission of a focused light beam through a liquid or gaseous light-absorbing substance contained in a vessel (e.g., a cuvette or microplate well) and the detection of the unabsorbed transmitted light by a light detector to measure the light absorption (or optical density) of the substance, thereby providing a measurement which can be related to the presence and amount of light absorbing matter in the liquid. U.S. Pat. No. 5,073,029 discloses several such opto-electronic devices and is incorporated herein by reference.

Figure 1:
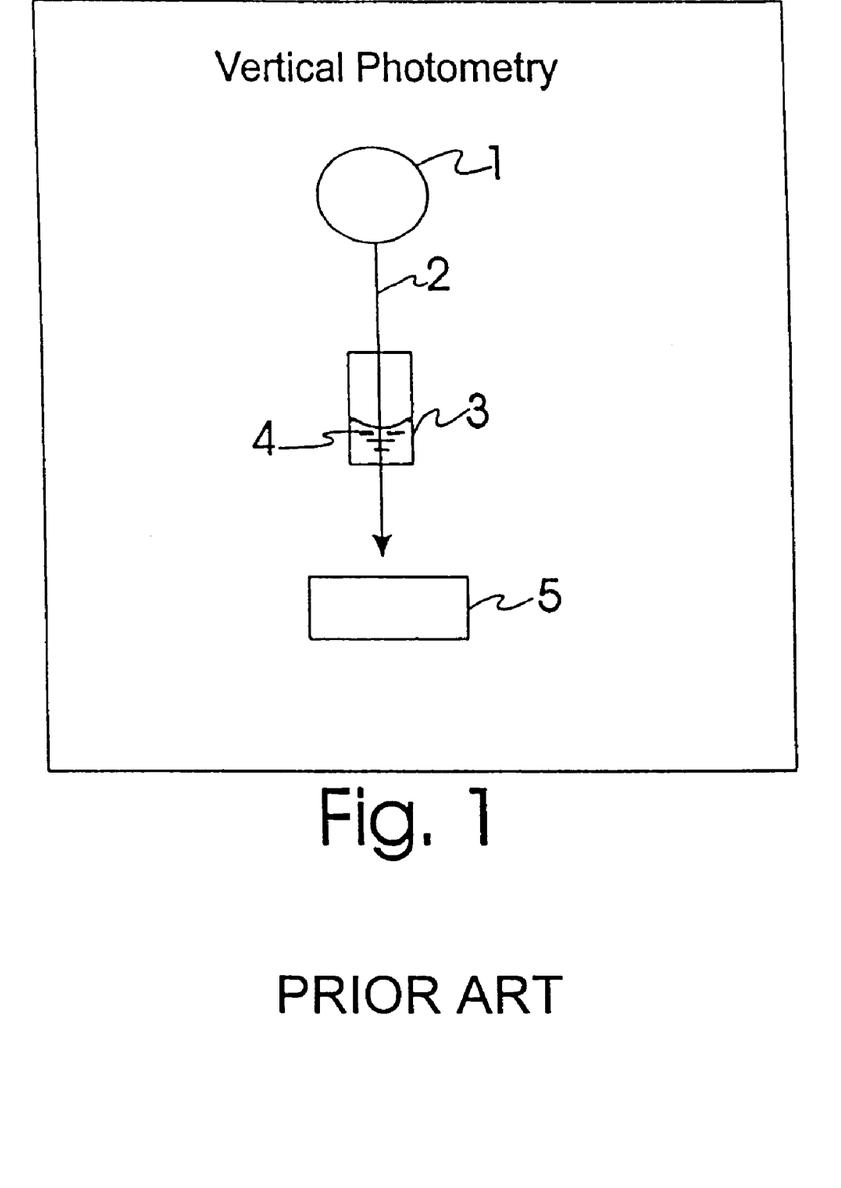
FIG. 1 is a representative cross sectional view of an apparatus for performing vertical spectrophotometry of a solution in accordance with the conventional methodology.

In conventional vertical beam photometry for performing spectrophotometric determinations (hereinafter, vertical spectrophotometry) as shown in FIG. 1, a light beam 2 emitted from a light source 1 is transmitted in the vertical direction along a vertical axis of the vessel 3 containing the solution 4 to be analyzed. The light absorption of the solution 4 is then measured by a detector 5 at the opposite end of the vessel positioned to receive the light beam 2 after it passes through the solution 4. Examples of such vertical spectrophotometric equipment include the SPECTRAMAX PLUS and the VMAX KINETIC READER from MOLECULAR DEVICES CORP., and the POWER WAVE 200 and EL310 ELISA MICROPLATE READER from BIO-TEK INSTRUMENTS, INC.

Figure 2:
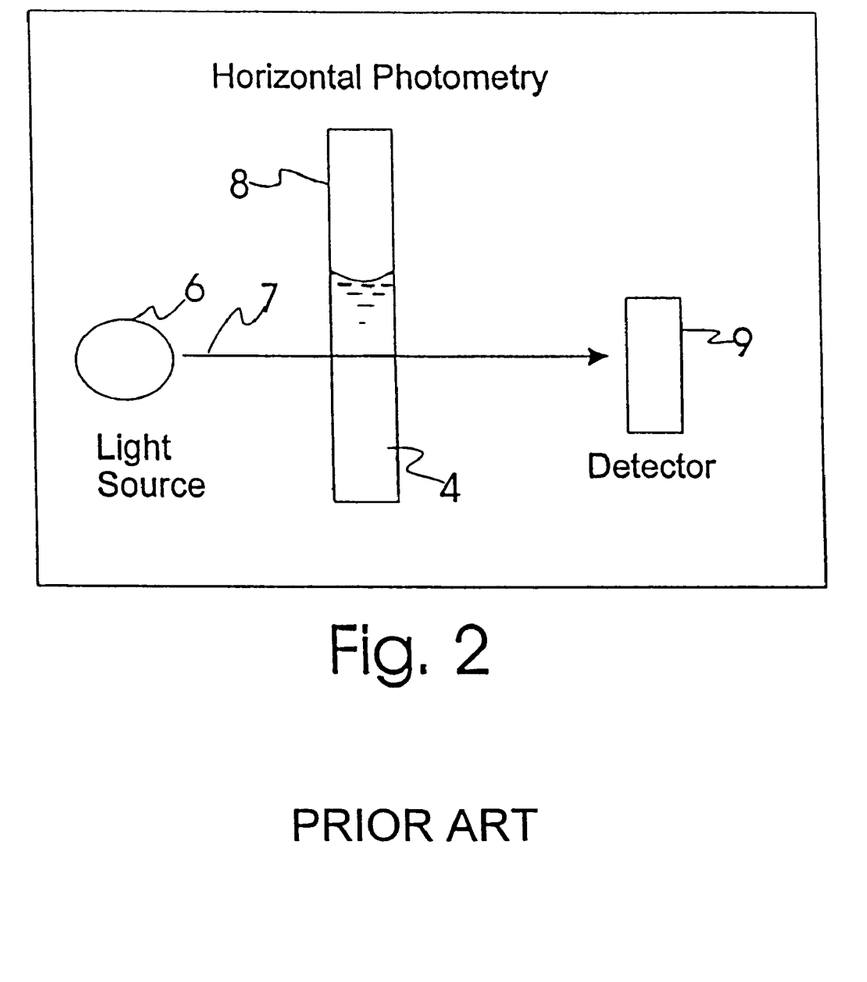
FIG. 2 is a representative cross sectional view of an apparatus for performing horizontal spectrophotometry of a solution in accordance with the conventional methodology.

In horizontal beam photometry for performing spectrophotometric determinations (hereinafter, horizontal spectrophotometry) as shown in FIG. 2, the light beam 7 emitted from a light source 6 is transmitted along a horizontal path which is at a right angle to the vertical axis of the vessel 8 containing the solution 4. The absorption of the light is then measured by a detector 9 at the opposite side of the vessel positioned to receive the light beam 7 after it passes through the solution 4. Examples of such horizontal spectrophotometric equipment include the SPECTRONIC GENESYS 5 by SPECTRONICS INSTRUMENTS, INC., and the SHIMADZU UV1201 by SHIMADZU, INC. spectrophotometers.

In horizontal spectrophotometry, the use of specific fixed light pathlength distances (e.g., 1 cm) have become customary in order to directly compare results from different instruments and solutions. This has led to the generation of tabular information relating light absorption measurements with the concentration of specific known substances, thus, allowing the direct determination of the concentration of certain elements in a sample of the tested substance based on its absorption at a specific wavelength of light. Because the vessel containing the substance has a fixed cross sectional dimension (e.g., inner diameter) which sets the light beam pathlength distance, highly precise absorption measurements can be made using horizontal spectrophotometry.

However, unlike horizontal spectrophotometry, in vertical spectrophotometry, as in the case where substances are tested in microplate wells, the distance that the light travels through the light absorbing substance, or the pathlength, varies and is dependent upon the volume of the substance, as well as a number of other factors such as the surface tension properties of the solution which can create variations in the meniscus formed in the vessel. These factors result in a high degree of variability in the light beam pathlength for any given sample substance, and, as a result, the resulting absorption determination can be imprecise. Furthermore, with the increased use of newer vessels having smaller well volumes as in the case of microplates with 364 or more wells, the physical properties of the liquid-solid interaction become more pronounced increasing the error percentage in any given reading using vertical spectrophotometry.

In order to overcome the imprecision associated with vertical spectrophotometry, prior art solutions include treating the inside surface of the vessel with a surfactant in order to minimize problems associated with surface tension, thereby reducing the variability in the meniscus formed in the sample vessel. For example, U.S. Pat. No. 4,741,619 (incorporated herein by reference) discloses making the walls of a microplate hydrophilic by treating them with surfactant so as to reduce the curvature of the meniscus obtained in the center of the wells that is perpendicular to the vertical light beam. Accordingly, the well to well variability of the meniscus is minimized, thereby improving the reliability of vertical beam spectrophotometric measurements.

While treating the well walls with a surfactant may decrease the variability in the meniscus, the process does not eliminate the meniscus effect nor is it compatible with all light-absorbing substances. Furthermore, attempts to reduce variability in the meniscus do not address variability in the total volume of the is sample. Thus, the determination of the exact light beam pathlength, which is critical for the direct conversion of an absorption measurement to a concentration value, is often difficult as a result of the indeterminate liquid surface level.

Other attempts to overcome the problems associated with conventional vertical spectrophotometry include combining vertical and horizontal spectrophotometry to accomplish the task of determining the pathlength of solutions in microplate wells. In these instances a horizontal spectrophotometric measurement is made of a light absorbing solution contained in a vessel of known dimensions and then compared to the determination made from a vertical spectrophotometric measurement. The SPECTROMAX PLUS is an example of a product that performs this task. However, there exist several problems with this comparison methodology. First, the methodology does not prevent variation as a result of surface tension which causes a meniscus to form on the surface of the liquid-air interface. Furthermore, the methodology introduces additional variability by the use of separate optical paths for vertical and horizontal spectrophotometric measurements.

As the microplate industry has grown and developed, the need for more accurate vertical spectrophotometric determinations has increased. The present invention addresses this need for accurately determining the absorption characteristics of a substance using vertical spectrophotometric measurements by performing these measurements on the basis of a known fixed light beam pathlength of the analyzed substance.

SUMMARY OF THE INVENTION

It is a general object of the invention to provide an accurate method of measuring the light absorbance or transmittance of a substance. It is also an object of the present invention to provide an accurate method of measuring the light absorbance or transmittance of a substance using vertical spectrophotometry by transmitting a light beam through a substance over a known fixed light beam pathlength.

It is also an object of the present invention to provide an apparatus which allows vertical spectrophotometry by transmitting a light beam through a substance over a known fixed light beam pathlength.

The above objects are achieved by employing a method of performing optical density measurements using vertical spectrophotometry to determine the presence of an analyte in a substance contained within a vessel, the vessel including a containment portion for accommodating the substance which is to be analyzed, the containment portion having an upper surface and a lower surface spaced apart from one another by a distance corresponding to a known fixed light beam pathlength; and the vessel further including an overfill/spout having an opening above the upper surface, the spout communicating with the containment portion for supplying the substance to the containment portion; comprising the steps of:

(a) filling the containment portion of the vessel with the substance so that the substance completely occupies the containment portion between the upper surface and the lower surface which define the known fixed light beam pathlength;

(b) transmitting a light beam through the upper surface, the lower surface, and the substance which occupies the containment portion between the upper surface and the lower surface; and (c) detecting the transmitted light beam after the transmitted light beam is transmitted through the lower surface.

The above objects are also achieved by performing vertical spectrophotometry using a vessel adapted for performing optical density measurements of a substance comprising:

a containment portion for accommodating the substance which is to be analyzed using vertical spectrophotometry, the containment portion having an upper surface and a lower surface spaced apart from one another by a distance defining a known fixed light beam pathlength; and a spout having an opening above the upper surface, the spout communicating with the containment portion for supplying the substance to the containment portion.

The method and apparatus of the present invention are based on a vessel having a fixed light beam pathlength for vertical spectrophotometry and, thus, eliminates the variability in pathlengths and uncertainty in absorbance determinations associated with conventional vertical spectrophotometry wherein the light beam pathlengths vary due to the different volumes of the analyzed substances as well as a number of other factors such as the surface tension properties of the analyzed substances.

BRIEF DESCRIPTION OF THE DRAWINGS

The above and other objects of the present invention can be better understood with reference to the following detailed description of the specific embodiments when considered in combination with the drawings that form part of the specification, wherein:

FIG. 6 is a representative top view of the apparatus and adapter illustrated in FIG. 5a.

DETAILED DESCRIPTION OF PREFERRED EMBODIMENTS

Figure 3:
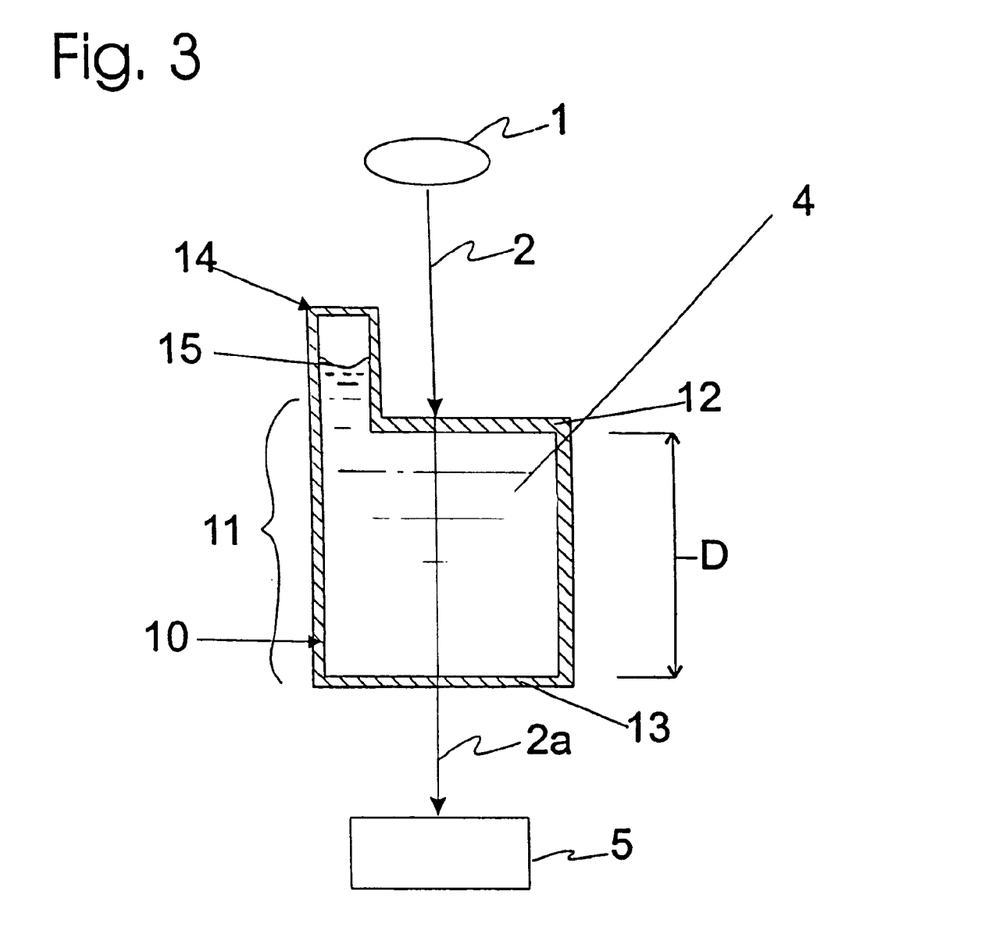
FIG. 3 is a representative cross sectional view of an apparatus for performing vertical spectrophotometry of a solution in accordance with an embodiment of the present invention.

FIG. 3 illustrates a setup for performing vertical spectrophotometric analysis on a light absorbing substance/solution 4 in accordance with an embodiment of the invention. The vessel 10 has a containment portion 11 defined in part by a transparent upper surface 12 and a transparent lower surface 13 which are spaced apart at a predetermined distance corresponding to a fixed light beam pathlength D. A spout (or an overfill portion) 14 in communication with the containment portion 11 is disposed on the vessel so that its opening is positioned above the upper surface 12. Accordingly, the spout 14 can be used to introduce the light-absorbing substance into the containment portion.

As shown in FIG. 3, the light source 1 is positioned above the vessel 10 so that the vertical beam of light 2 emitted from the light source 1 is directed to be transmitted through the transparent upper surface 12 of the containment portion 11, through the solution 4 within the containment portion 11, and through the transparent lower surface 13 of the containment portion 11 without interference from the spout 14. Accordingly, the portion of the light beam 2a which is not absorbed by the substance 4 is detected by the detector 5. In the preferred embodiment of the apparatus, the upper surface 12 and the lower surface 13 are parallel to one another. The light beam 2a which passes through the lower surface 13 is measured by the detector 5 disposed below the lower surface 13 and opposite the light source 1.

In the configuration of FIG. 3, the light path is directed vertically, however, the physical dimensions of the containment portion define the fixed light beam pathlength D of the substance 4. Moreover, the liquid-air interface 15 is located in the spout 14 which is offset from the path of the vertical light beam so as not to factor into the light absorbance measurement.

Figure 4:
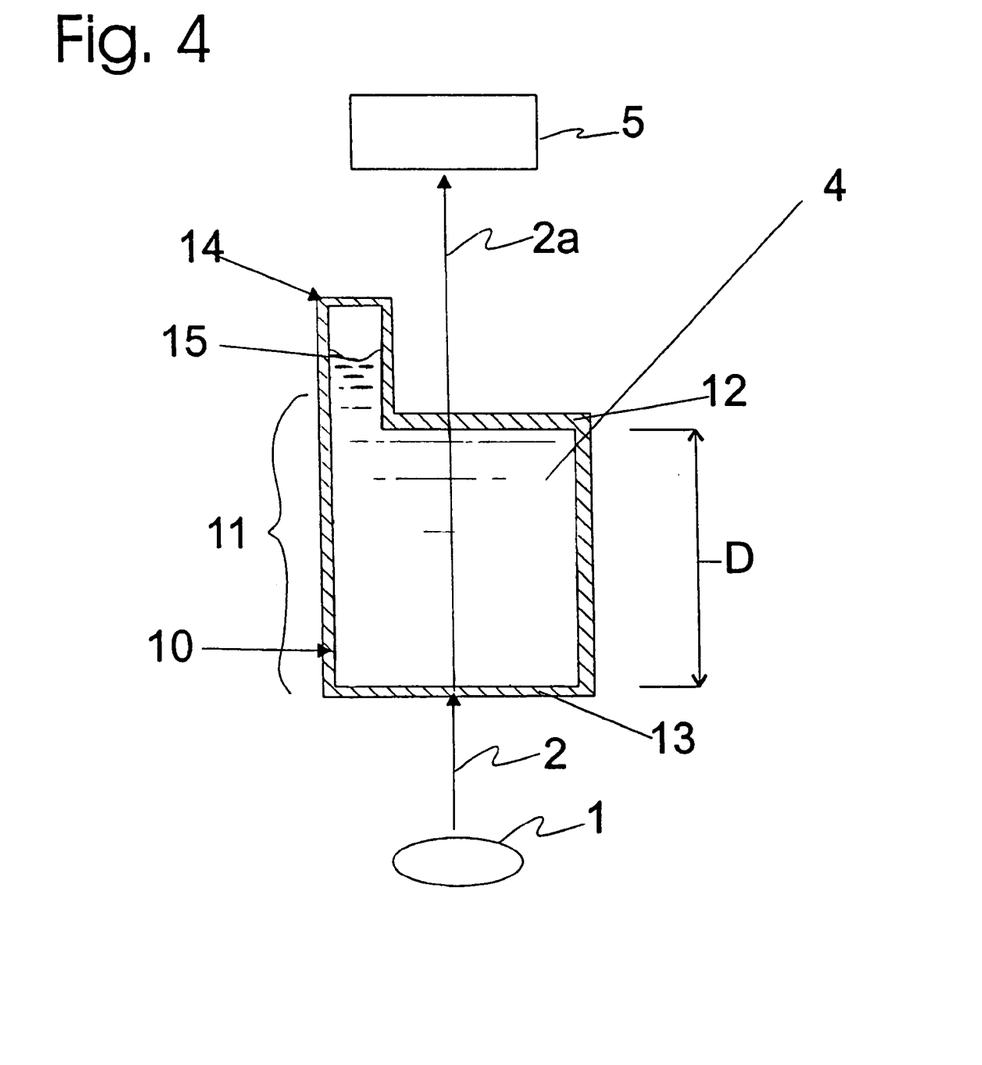
FIG. 4 is a representative cross sectional view of an apparatus for performing vertical spectrophotometry of a solution in accordance with another embodiment of the present invention.

While the above configuration places the light source 1 above the vessel, alternative configurations are possible. For example, as shown in FIG. 4, the light source 1 can be positioned below the sample and the detector 5 can be positioned above the sample.

Figure 5A:
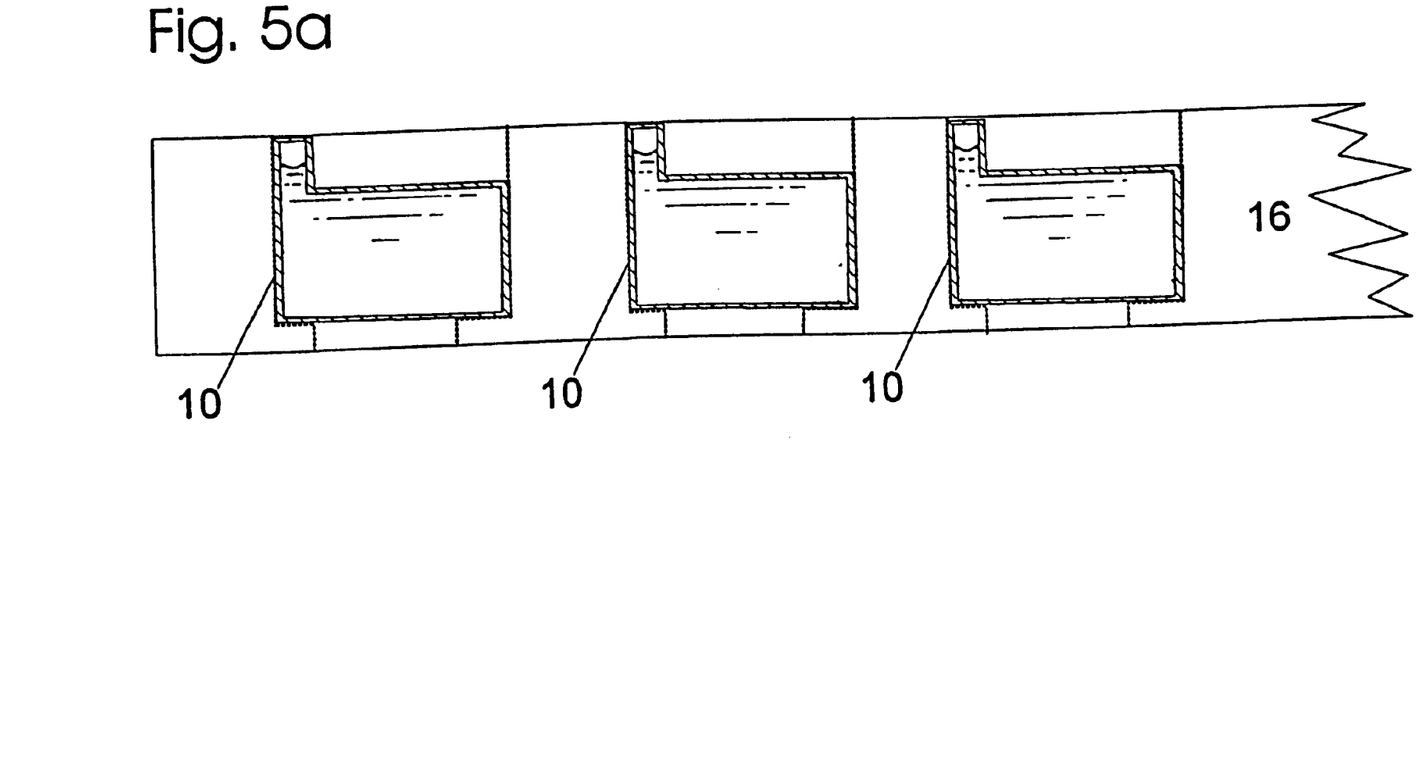
FIGS. 5a–5b are representative cross sectional views of an apparatus for performing vertical spectrophotometry of a solution and an adapter for supporting the apparatus in accordance with another embodiment of the present invention.
Figure 5B:
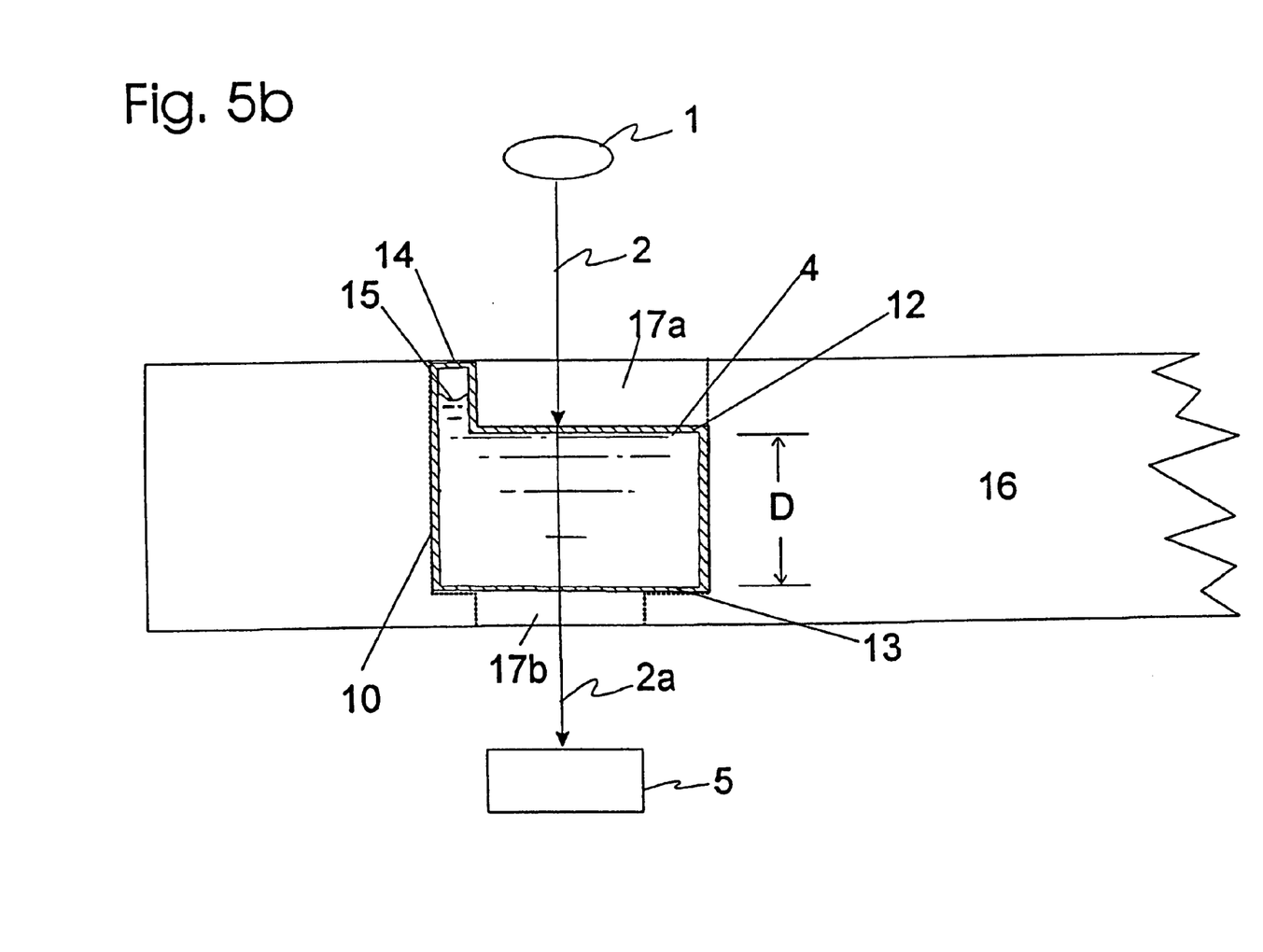
Figure 6:
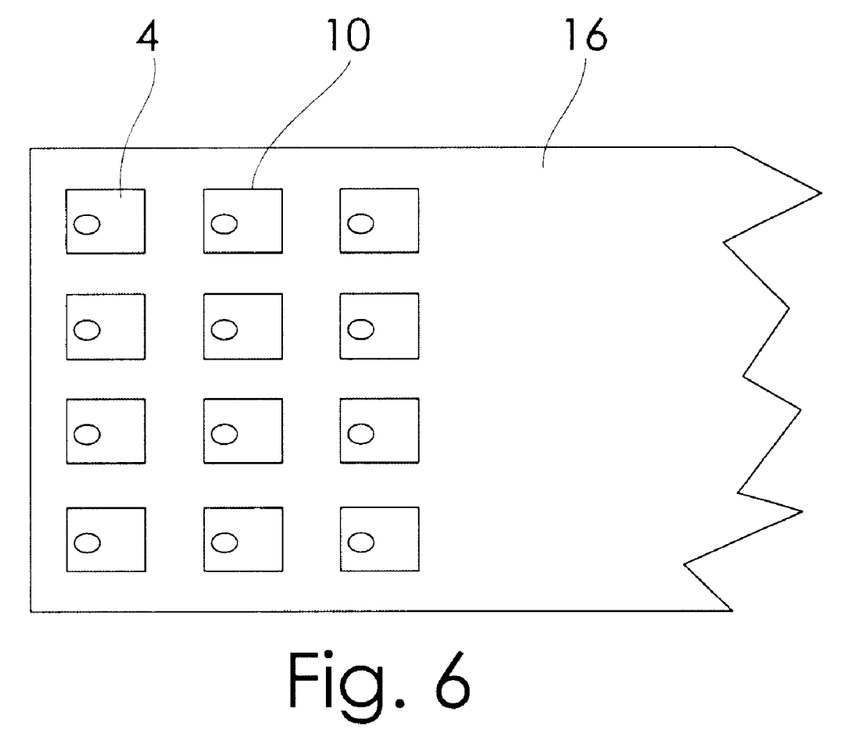

FIGS. 5a, 5b, and 6 illustrate another embodiment of the invention wherein the vessel is placed in an adapter which allows vertical spectrophotometric measurements of fixed pathlengths in a conventional microplate reader. Conventional microplate readers as, for example, those described in U.S. Pat. No. 5,073,029 (incorporated herein by reference), are adapted to perform vertical spectrophotometric measurements of substances or samples contained in standard microplate wells which are arranged in a strip or in-line format, or in a matrix format. Common microplate well configurations include the 96-well plate which has an 8×12 well matrix, and the 384-well plate having a 16×24 well matrix. Therefore, in order to allow one to perform vertical spectrophotometric measurements of fixed pathlengths in a conventional microplate reader, an adapter is needed which accommodates the vessels described above which have known fixed pathlengths and which can itself be accommodated in the conventional microplate reader.

As shown in FIGS. 5a–5b, the light source 1 illuminates the vessel 10 containing the light-absorbing substance 4. The vessel 10 rests in an adapter 16 that allows the device to be used in a conventional microplate reader (not shown). An illuminating light beam 2 emitted from the light source 1 passes through an opening 17a located in the upper part of the adapter 16, through the vessel 10 containing light absorbing substance 4, and through another opening 17b located in the bottom of the adapter 16. The thus transmitted light beam 2a is measured by the detector 5 located below the vessel 10 and opposite the light source 1. The spout 14 is offset from the path of light beam 2 allowing measurements of the light absorbing substance to be made through the transparent upper surface 12 and transparent lower surface 13 of the vessel 10. As described in the first embodiment, the upper surface 12 and the lower surface 13 are parallel to one another and perpendicular to the axis of the light beam 2. While FIG. 5a illustrates only three vessels 10 present in the adapter 16, it is understood by those skilled in the art that any number of adapters can be accommodated, limited only by the size and capabilities of the microplate reader for which the adapter is configured. It is preferred, however, that the adapter be configured so that the vessels held therein correspond to specific microplate well locations for standard microplates. Furthermore, while vessels illustrated in the figures have a rectangular shape, the invention is not limited to this shape.

Figure 7:
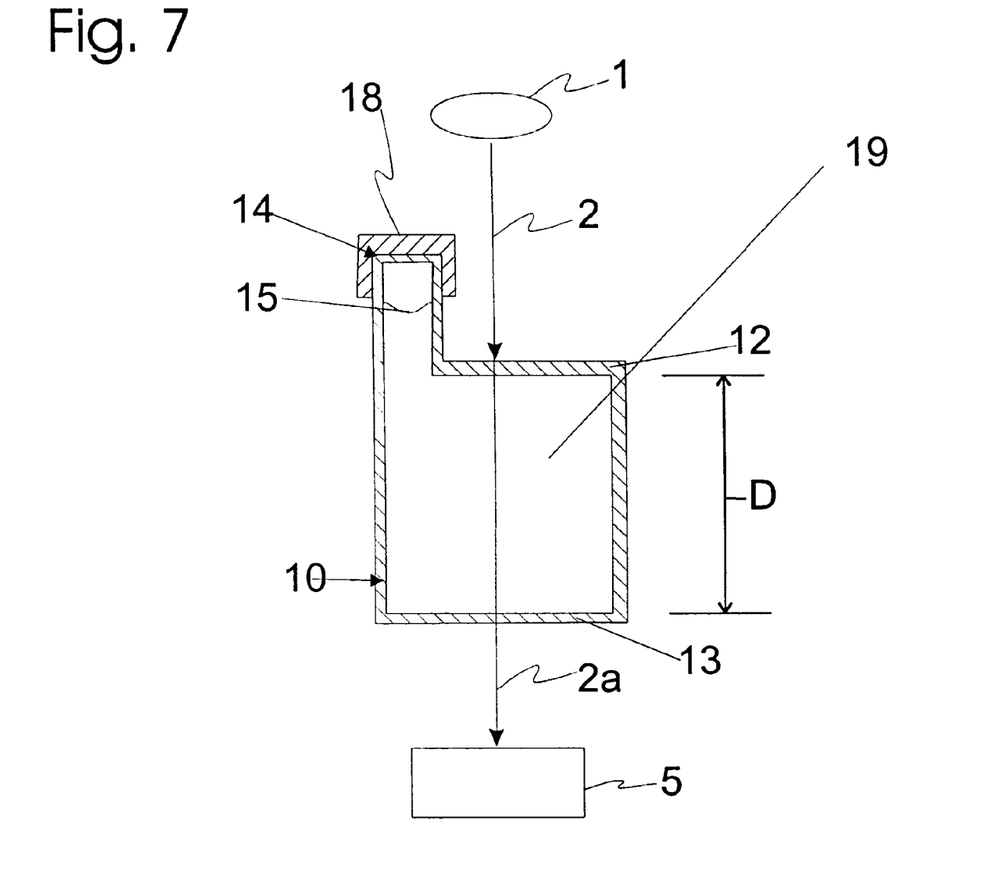
FIG. 7 is a representative cross sectional view of the apparatus of FIG. 3 including a cap for a spout for containing a volatile substance within a vessel.

In another embodiment as shown in FIG. 7, a cap 18 can be provided for sealing the spout 14 so that volatile or gaseous substances 19 introduced into the vessel 10 cannot escape. Again, since the spout and cap are positioned outside the path of the light beam 2, they do not interfere with the measurement of the light absorbance of the substance 19.

As described above, when performing vertical spectrophotometric measurements in accordance with the present invention, the distance (or pathlength) that a light beam travels through the analyzed substance remains known and fixed by the upper and lower surfaces, thereby allowing one to utilize the readings on the light absorbance or optical density of the analyzed substance with the tabulated information relating light absorption measurements with the concentration of specific elements to determine concentrations of the analyzed substance. For example, by using a vessel which has a pathlength set to be 1 cm, an operator can measure the absorbance of a substance contained within the vessel and by referring to the tabulated values defined for a pathlength of 1 cm as shown in Table 1 below, determine the concentration of the substance.

TABLE 1

| Nucleic Acids | Concentration for 1 $A_{260}$ unit |
|---|---|
| DNA (double stranded) | 50 g/ml |
| RNA (single stranded) | 33 g/ml |
| DNA (single stranded) | 40 g/ml |
| Proteins | $A_{280}$ units for 1 mg/ml solution |
| IgG | 1.35 |
| IgM | 1.2 |
| IgA | 1.3 |
| Protein A | 0.17 |
| Avidin | 1.5 |
| Streptavidin | 3.4 |
| Bovine serum albumin | 0.7 |
| Miscellaneous | $A_{340}$ units for 0.1 mg/ml solution |
| NADH | 0.8 |
| NADPH | 0.8 |

Accordingly, the errors in the readings using the conventional method caused by the variability in the volume of the analyzed substance as well as the variability in the surface tension properties of the analyzed substance are eliminated.

It is contemplated that numerous modifications may be made to the method of and apparatus for measuring the optical density of a substance using a vessel having a known fixed light beam pathlength of the present invention without departing from the spirit and scope of the invention as defined in the following claims.

What is claimed is:

1. A vessel for use in performing optical density measurements of a substance using vertical spectrophotometry to determine the presence of an analyte in the substance, comprising:

a containment portion for accommodating the substance which is to be analyzed using vertical spectrophotometry, said containment portion having an upper surface and a lower surface spaced apart from one another by a distance defining a known fixed light beam pathlength; and a spout having an opening above said upper surface, said spout communicating with said containment portion for supplying the substance to said containment portion, and wherein said vessel is a detached vessel so as to be capable of separate handling by an operator.

2. The vessel for use in performing optical density measurements of a substance in accordance with claim 1, wherein said spout is disposed so as not to interfere with a vertical light beam transmitted through said upper and lower surfaces when performing optical density measurement using vertical spectrophotometry.

3. The vessel for use in performing optical density measurements of a substance in accordance with claim 1, wherein said upper surface is parallel to said lower surface.

4. The vessel for use in performing optical density measurements of a substance in accordance with claim 1, wherein said upper surface and said lower surface are transparent so as to permit light to be transmitted therethrough.

5. The vessel for use in performing optical density measurements of a substance in accordance with claim 1, wherein said spout further comprises a cap for sealing said spout opening.

6. The vessel for use in performing optical density measurements of a substance in accordance with claim 5, wherein said cap is adapted to contain volatile liquid substances.

7. The vessel for use in performing optical density measurements of a substance in accordance with claim 5, wherein said cap is adapted to contain gaseous substances.

8. An apparatus for performing optical density measurements of a substance using a microplate reader for conducting vertical spectrophotometry to determine the presence of an analyte in the substance, comprising:

a vessel;

a containment portion within said vessel for accommodating the substance which is to be analyzed using vertical spectrophotometry, said containment portion having an upper surface and a lower surface spaced apart from one another by a distance defining a known fixed light beam pathlength;

a spout connected to said vessel having an opening above said upper surface, said spout communicating with said containment portion for supplying the substance to said containment portion; and an adapter having a recess for accommodating said vessel within the microplate reader, said recess including an upper portion and lower portion corresponding to the upper surface and lower surface of said containment portion, respectively, for allowing a transmission of light through said adapter and said containment portion.

9. The apparatus for performing optical density measurements of a substance using a microplate reader in accordance with claim 8, wherein said adapter has a plurality of recesses for accommodating a respective plurality of vessels.

10. The apparatus for performing optical density measurements of a substance using a microplate reader in accordance with claim 9, wherein said plurality of recesses are located within said adapter so that respective centers of said plurality of recesses align with respective centers of corresponding well positions on a standard microplate.

11. A vessel for use in performing optical density measurements of a substance using vertical spectrophotometry to determine the presence of an analyte in the substance, comprising:

a containment portion for accommodating the substance which is to be analyzed using vertical spectrophotometry, said containment portion having an upper surface and a lower surface spaced apart from one another by a distance defining a known fixed light beam pathlength;

a spout having an opening above said upper surface, said spout communicating with said containment portion for supplying the substance to said containment portion, and a cap for sealing said spout opening.

12. The vessel for use in performing optical density measurements of a substance in accordance with claim 11, wherein said cap is adapted to contain volatile liquid substances.

13. The vessel for use in performing optical density measurements of a substance in accordance with claim 11, wherein said cap is adapted to contain gaseous substances.

14. A vessel for use in performing optical density measurements of a substance using vertical spectrophotometry to determine the presence of an analyte in the substance, comprising:

a containment portion for accommodating the substance which is to be analyzed using vertical spectrophotometry, said containment portion having an upper surface and a lower surface spaced apart from one another by a distance defining a known fixed light beam pathlength; and a spout having an opening above said upper surface, said spout communicating with said containment portion for supplying the substance to said containment portion, and wherein said known fixed light beam pathlength is 1 cm.

15. A vessel for use in performing optical density measurements of a substance using vertical spectrophotometry to determine the presence of an analyte in the substance, comprising:

a containment portion for accommodating the substance which is to be analyzed using vertical spectrophotometry, said containment portion having an upper surface and a lower surface spaced apart from one another by a distance defining a known fixed light beam pathlength; and an overfill portion disposed above said upper surface, said overfill portion communicating with said containment portion, and wherein said vessel is a detached vessel so as to be capable of separate handling by an operator.

16. An apparatus for performing optical density measurements of a substance using a microplate reader for conducting vertical spectrophotometry to determine the presence of an analyte in the substance, comprising:

a vessel;

a containment portion within said vessel for accommodating the substance which is to be analyzed using vertical spectrophotometry, said containment portion having an upper surface and a lower surface spaced apart from one another by a distance defining a known fixed light beam pathlength;

an overfill portion disposed above said upper surface, said overfill portion communicating with said containment portion; and an adapter having a recess for accommodating said vessel within the microplate reader, said recess including an upper portion and lower portion corresponding to the upper surface and lower surface of said containment portion, respectively, for allowing a transmission of light through said adapter and said containment portion.

17. A method of performing optical density measurements using vertical spectrophotometry to determine the presence of an analyte in a substance contained within a vessel, comprising the steps of:

(a) providing a vessel including a containment portion for accommodating the substance which is to be analyzed, the containment portion having an upper surface and a lower surface spaced apart from one another by a distance defining a known fixed light beam pathlength; and the vessel further including a spout having an opening above the upper surface, the spout communicating with the containment portion for supplying the substance to the containment portion;

(b) filling the containment portion of the vessel with the substance so that the substance completely occupies the containment portion between the upper surface and the lower surface;

(c) transmitting a light beam through the upper surface, the lower surface, and the substance which occupies the containment portion between the upper surface and the lower surface;

(d) detecting the transmitted light beam after the transmitted light beam is transmitted through the lower surface, thereby determining the amount of light absorbed by the substance.

18. A method of performing optical density measurements using vertical spectrophotometry to determine the presence of an analyte in a substance contained within a vessel, comprising the steps of:

(a) providing a vessel including a containment portion for accommodating the substance which is to be analyzed, the containment portion having an upper surface and a lower surface spaced apart from one another by a distance defining a known fixed light beam pathlength; and the vessel further including a spout having an opening above the upper surface, the spout communicating with the containment portion for supplying the substance to the containment portion;

(b) filling the containment portion of the vessel with the substance so that there is a fixed predetermined pathlength for the substance within said containment portion;

(c) transmitting a light beam through the upper surface, the lower surface, and the substance which occupies the containment portion between the upper surface and the lower surface;

(d) detecting the transmitted light beam after the transmitted light beam is transmitted through the lower surface, thereby determining the amount of light absorbed by the substance.

19. A method of performing optical density of a substance using a microplate reader for conducting vertical spectrophotometry to determine to determine the presence of an analyte in a substance contained within a vessel, comprising the steps of:

(a) providing a vessel including a containment portion for accommodating the substance which is to be analyzed, the containment portion having an upper surface and a lower surface spaced apart from one another by a distance defining a known fixed light beam pathlength; the vessel further including a spout having an opening above the upper surface, the spout communicating with the containment portion for supplying the substance to the containment portion;

(b) providing an adapter having a recess for accommodating the vessel within the microplate reader, the recess including an upper portion and a lower portion corresponding to the upper surface and the lower surface of the containment portion, respectively, for allowing a transmission of light through the adapter;

(c) filling the containment portion of the vessel with the substance so that the substance completely occupies the containment portion between the upper surface and the lower surface;

(d) placing the vessel in the adapter for conducting optical density measurements with the microplate reader;

(e) transmitting a light beam through the upper surface, the lower surface, and the substance which occupies the containment portion between the upper surface and the lower surface;

(f) detecting the transmitted light beam after the transmitted light beam is transmitted through the lower surface, thereby determining the amount of light absorbed by the substance.

20. A method of performing optical density measurements using vertical spectrophotometry to determine the presence of an analyte in a substance contained within a vessel, comprising the steps of:

(a) providing a vessel including a containment portion for accommodating the substance which is to be analyzed, the containment portion having an upper surface and a lower surface spaced apart from one another by a distance defining a known fixed light beam pathlength; and the vessel further including an overfill portion disposed above the upper surface, the overfill portion communicating with the containment portion;

(b) filling the containment portion of the vessel with the substance so that there is a fixed predetermined pathlength for the substance within said containment portion;

(c) transmitting a light beam through the upper surface, the lower surface, and the substance which occupies the containment portion between the upper surface and the lower surface;

(d) detecting the transmitted light beam after the transmitted light beam is transmitted through the lower surface, thereby determining the amount of light absorbed by the substance.

* * * * *